US005437686A

United States Patent [19]

Heffner et al.

[11] Patent Number: 5,437,686

[45] Date of Patent: Aug. 1, 1995

[54] PEROXYGEN BLEACH COMPOSITION ACTIVATED BY BI AND TRICYCLIC DIKETONES

[75] Inventors: Robert J. Heffner; Robert J. Steltenkamp, both of Somerset, N.J.

[73] Assignee: Colgate-Palmolive Co., New York, N.Y.

[21] Appl. No.: 245,317

[22] Filed: May 18, 1994

[51] Int. Cl.$^6$ .......... C07C 49/303; C11D 3/20; C11D 3/395; D06L 3/02

[52] U.S. Cl. .......... 8/111; 8/137; 252/95; 252/99; 252/174.14; 252/186.38; 252/DIG. 14; 568/373; 568/374

[58] Field of Search .......... 252/95, 99, 174.14, 252/186.38; 8/111, 137; 568/373, 374

[56] References Cited

U.S. PATENT DOCUMENTS

| | | | |
|---|---|---|---|
| 4,001,131 | 1/1977 | Montgomery | 252/99 |
| 4,167,577 | 9/1979 | Marquez | 424/273 P |
| 4,421,664 | 12/1983 | Anderson | 252/94 |
| 4,551,263 | 11/1985 | Schelhammer | 252/186.39 |
| 4,973,418 | 11/1990 | Hodge | 252/102 |
| 5,055,217 | 10/1991 | Garcia | 252/94 |
| 5,069,812 | 12/1991 | Humphreys | 252/186.44 |
| 5,366,593 | 11/1994 | Lee | 162/72 |

*Primary Examiner*—Dennis Albrecht
*Attorney, Agent, or Firm*—Bernard Lieberman; Robert C. Sullivan

[57] ABSTRACT

Bleaching compositions comprising an inorganic peroxygen compound and a bicyclic or tricyclic diketone as an activator for the peroxygen compound. The composition preferably comprises about 1 to about 75% of the peroxygen bleaching compound and about 1 to about 75% of the bicyclic or tricyclic diketone bleaching compound activator. The conventional additives such as surfactants, antifoaming agents, fabric softeners, stablizers, inorganic builder salts, buffers, enzymes and the like may be present as indicated. The compositions can be formulated as dry concentrated, aqueous solutions, aqueous solutions containing non-aqueous solvents, etc. The compositions are environmentally safe, effective as bleaching agents from below room temperature to higher temperatures, biodegradable and otherwise highly desirable.

27 Claims, No Drawings

PEROXYGEN BLEACH COMPOSITION ACTIVATED BY BI AND TRICYCLIC DIKETONES

The instant invention relates to bleaching compositions containing a peroxygen bleaching compound and a bicyclic or tricyclic diketone. In aqueous solution and at room temperature or higher temperatures the peroxygen bleaching compound is activated to form a dioxirane. More particularly this invention relates to bleaching compositions comprising a mixture of a monopersulfate peroxygen bleaching compound and a bicyclic or tricyclic diketone bleach activator which react together in aqueous solution to form a dioxirane bleaching composition.

BACKGROUND OF THE INVENTION

Bleaching compositions are used in the home and in industrial applications for bleaching stains on hard surfaces and soiled fabrics. Hypochlorite bleaches are effective at removing stains, when used in relatively high concentrations, but hypochlorite, along with other active chlorine bleaches, cause rather severe damage to fabric colors as well as causing damage to the textile fibers. Additionally, hypochlorite liquid bleaches present handling and packaging problems. Color and fabric damage can be minimized by using milder oxygen bleaches such as sodium perborate or potassium monopersulfate. The stain removal characteristics of these peroxygen bleaches, however, are much less desirable than those of the harsher halogen bleaching agents. As a result, commercial bleaching compositions which contain peroxygen bleaches commonly utilize activators, i.e., compounds that enhance the performance of the peroxygen bleach. Bleaching compositions employing different types of bleach activators have been disclosed, for example, in: Poplin, U.S. Pat. No. 1,940,768, Dec. 26, 1933; Baevsky, U.S. Pat. No. 3,061,550, Oct. 30, 1962; MacKellar et al., U.S. Pat. No. 3,338,839, Aug. 29, 1967; and Woods, U.S. Pat. No. 3,556,711, Jan. 19, 1971.

The continuing attempt to find effective activators, other than those already present and employed in the art, include U.S. Pat. No. 3,822,114 which teaches a bleaching composition comprising a peroxygen bleaching compound and a ketone or aldehyde bleaching activator. U.S. Pat. No. 3,822,114 fails to provide an effective and user acceptable bleaching composition as the bleaching process cannot be carried out at room temperature requiring instead that the washing to remove fabric stains be carried out at temperatures in excess of 100° F.

Robert W. Murray in his article entitled "Dioxiranes," *Chem Rev.,* 1989, 1187–1201 describes the formation of dioxiranes from ketones and monopersulfates but fails to teach the ketal cycloalkanedione bleach activators disclosed in copending application Ser. No. 7/870,362 or the bicyclic or tricyclic diketone activators of the instant invention, which make possible the carrying out of room temperature bleaching of stained fabrics and hard surfaces.

Waldemar Adam et al., in Acc. Chem. Res. 1989, 22,205–211 teaches the formation of dioxiranes from monopersulfates and ketones but as in the case of Murray, the publication fails to disclose the criticality of the selection of the bleach activator if satisfactory bleaching results at room temperature are to be realized.

In copending patent application Ser. No. 7/870,362 assigned to the same assignee as the instant application, bleach activators representing an improvement over these previously disclosed for use in the cleaning of fabrics and hard surfaces are disclosed. The disclosed activators are capable of activating the peroxygen compound at room temperature while causing less damage to the fabric being cleaned. The bleach activators described in the aforesaid application are ketal cyclohexanediones and when admixed with the peroxygen compound allow the user to effectively remove stains and soil from fabrics and/or hard surfaces at room temperature.

It is an object of this invention to provide improved bleaching compositions for use in the room temperature bleaching and/or removal of stains from fabrics and hard surfaces.

It is a further object of the invention to provide new and enhanced activating agents for peroxygen bleaches.

It is still another object of the invention to provide improved concentrated, bleaching compositions for use alone or in combination with other conventional laundering adjuvants for enhanced removal of stains on fabrics or hard surfaces.

It has now been found that by combining a peroxygen bleaching agent with a bicyclic or tricyclic ketone as activator for the bleaching agent, improved compositions are obtained which accomplish the foregoing objects and are unexpectedly superior in their bleaching effectiveness to the compositions of the prior art.

The peroxygen bleaching compositions of the invention can be used directly in aqueous solution to bleach a fabric or a hard surface or in the alternative the bleaching compositions can be incorporated as an additive to a cleaning composition such as a powdered laundry detergent, a non aqueous laundry detergent, a scouring powder, a hard surface cleaning composition, a powdered automatic dishwashing composition, a nonaqueous automatic dishwashing composition, a hair bleaching composition, a wound cleansing composition, a dental cleansing composition, a paper bleaching composition, a prespotter and the like.

SUMMARY OF THE INVENTION

The present invention provides new and improved peroxygen bleaching compositions which are comprised of a peroxygen bleaching compound and a bicyclic or tricyclic diketone bleaching compound activator corresponding to the general formula:

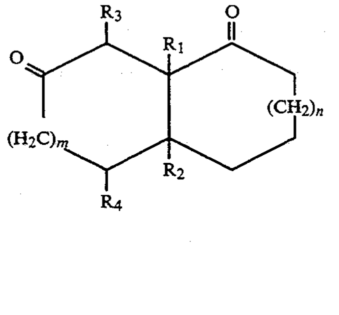

-continued

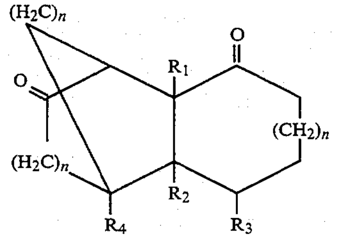

wherein $R_1$, $R_2$, $R_3$, and $R_4$ are each hydrogen, C1-8 alkyl, C6-12 aryl, C7-12 alkylaryl, halogen (fluorine, chlorine or bromine), or nitrogen, m is 0,1,2 or 3 and n is 0,1,2 or 3. The disclosed compositions can be used to bleach or clean fabric articles and hard surfaces at room temperature with substantially no damage resulting to the fabric or the surface being cleaned. The invention also provides cleaning compositions incorporating the aforesaid compositions into their formulations, a process for activation of the peroxygen compounds and methods for using the bleaching compositions.

DETAILED DESCRIPTION OF THE INVENTION

The instant invention is directed to peroxygen bleaching compositions, and bleaching and/or stain removal processes carried out in an aqueous solution utilizing the peroxygen bleaching compositions of the invention. The peroxygen bleach-activator combination, i.e., the bleaching composition of the invention finds utility in a plurality of major practical areas both in the home and industrially. For example, the bleaching compound-activator compositions can be used alone or in combination with other conventional ingredients to carry out (1) direct bleaching of stains on fabrics; (2) removal by bleaching of stains found on hard surfaces; and (3) inhibition of the transfer to fabric articles of solubilized or suspended dyes found in fabric laundering solutions.

The bleach compositions of the instant invention comprise a mixture of a peroxygen bleaching compound preferably a monoperoxysulfate and most preferably potassium monoperoxysulfate and a bicyclic or tricyclic diketone, more specifically a decalindione or a derivative thereof having the formula as shown above, as peroxygen bleach activator, in a weight ratio of peroxygen bleaching compound to peroxygen bleach activator of about 1:1 to about 100:1, more preferably about 1:1 to about 50:1, and most preferably about 1:1 to about 10:1.

The bleaching agents utilized in the instant composition are inorganic peroxygen salts, organic peroxygen acids and their water soluble salts. Examples of inorganic peroxygen salts include the water-soluble monopersulfates and water-soluble monoperoxyphosphates. Specific examples of such salts include sodium monopersulfate, potassium monopersulfate, disodium monoperphosphate and dipotassium monperphosphate. Highly preferred peroxygen salts, namely, those which are most highly activated by the activators utilized in the instant invention, are the sodium and potassium monopersulfates of the formulas $NaHSO_5$ and $KHSO_5$ respectively. Potassium monopersulfate is available commercially from E. I. dupont de Nemours and Company, Inc. under the trade name "Oxone". Oxone contains approximately 41.5% by weight $KHSO_5$ the balance being $KHSO_4$ and $K_2SO_4$ in about equal proportions.

Peroxyacids which are suitable for use in the present invention have the general formula

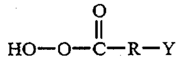

wherein R is an alkylene group containing from 1 to about 16 carbon atoms or an arylene group containing from 6 to about 8 carbon atoms and Y is hydrogen, halogen, alkyl, aryl or any group which provides an anionic moiety in aqueous solution. Y includes, for example,

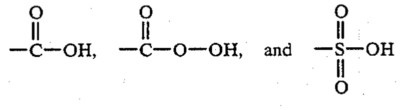

The organic peroxyacids or salts thereof suitable for use in the invention can contain either one or two peroxy groups and can be either aliphatic or aromatic. When the organic peroxyacid is aliphatic, the unsubstituted acid has the general formula

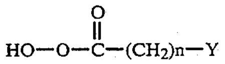

where Y, for example, can be

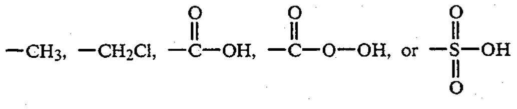

and n can be an integer of from 1 to 12, with perazelaic acids (n=7) being the preferred compounds. The alkylene linkage and/or Y group (if alkyl) can contain halogen or other non-interfering substituents. Examples of preferred aliphatic peroxyacids include diperazelaic acid and diperadipic acid.

When the organic peroxyacid is aromatic, the unsubstituted acid has the general formula

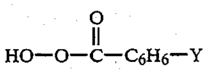

where Y is hydrogen, halogen, alkyl,

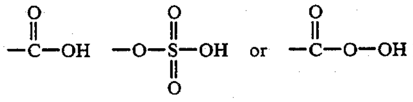

for example

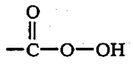

and the Y groups can be in any relative position around the aromatic ring. The ring and/or Y group (if alkyl) can contain non-interfering substituent such as halogen groups. Examples of suitable aromatic peroxy acids or salts thereof include monoperoxyphthalic acid, diperoxyterephthalic acid, 4-chlorodiperoxyphthalic acid and the monosodium salt of diperoxyterephthalic acid. Preferred aromatic peroxyacids are m-chloroperoxybenzoic acid and p-nitroperoxybenzoic acid. A highly preferred aromatic peroxyacid is diperoxyisophthalic acid. Mixtures of the peroxygen salt compounds and the peroxyacids can also be employed in the instant invention.

The concentration of the peroxygen bleaching compound in the compositions of the invention is about 1 to about 75wt. %, preferably about 5 to about 60 wt. %, and most preferably about 5 to about 50 wt. %. The concentration of the peroxygen bleaching compound is of a sufficient level in the composition to provide about 1 ppm to about 1000 ppm, when the composition is contacted with and dissolved in water at room temperature or higher.

The peroxygen bleach activator compounds of the instant invention have a formula selected from the group of:

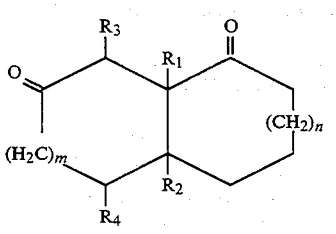

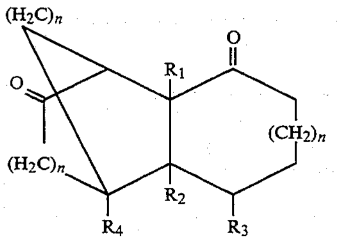

wherein $R_1$, $R_2$, $R_3$ and $R_4$ are each hydrogen, $C_{1}1 \propto C_{8}$ alkyl, $C_6$–$C_{12}$ aryl, $C_{9-2}$ alkylaryl, halogen (fluorine, bromine or chlorine), or nitrogen and can be at any ring junction in any combination; m is 0,1,2 and 3 and n is 0,1,2 or 3. Preferably alkyl has 1 to 6 carbon atoms, and arylalkyl has 7 to 10 carbon atoms. The diketone functions can be at any position on the cyclic structure in any combination. Three examples of preferred bicyclic and tricyclic diketones are the decalin-1, 5-dione(formula 3), methyldecalin-1, 6-dione (formula 4) and the tricyclic dione(formula 5). (See formulas below) The most preferred peroxygen bleach activators are those that have a melting point of at least 25° C. at one atmospheric pressure.

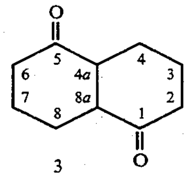

3

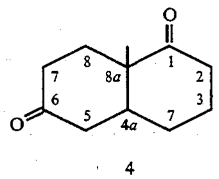

4

-continued

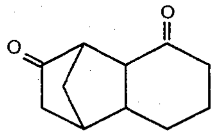

+ Isomers

5

Unlike the case of a chlorine containing bleach, for example, sodium hypochlorite, the reaction mechanism of the bleach system is an oxygen donating mechanism giving rise to a dioxirane intermediate when the composition comprised of the bleaching compound and bleach activator are contacted with water at room temperature or higher.

The mechanism can be generally depicted as:

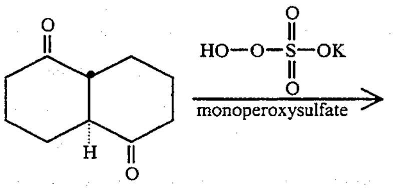

Decalindione

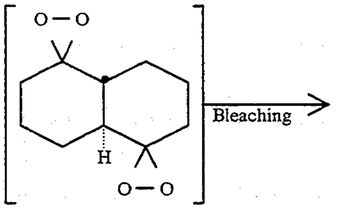

Dioxirane intermediate

The peroxygen bleach compound reacts with the decalindione peroxygen bleach activator upon contact with water to form the dioxirane bleaching agent. It is believed that during the bleach process the dioxirane intermediate reverts back to the original diketone, therefore behaving like a catalyst.

The peroxygen bleach activators of the instant invention as previously mentioned have a melting point of at least 25° C. which permits the dry solid peroxygen bleach activators, unlike liquid peroxygen bleach activators, to be readily post dry blended with the peroxygen bleaching compound. Additionally, the peroxygen bleach activators of the instant invention have the advantage that they are fully activated in the presence of water over a broad temperature range from below room temperature to higher temperature conditions; are stable solids resistant to hydrolysis; and are biodegradable leaving no nitrogen residue and thus are environmentally safe and acceptable. Further, the decalindiones as above described outperform the current state of the art bleach activators including those disclosed in copending application Ser. No. 7/870,362.

The concentration of the formed dioxirane in the water in use is about 1 to about 10,000 parts per million (ppm), more preferably about 1 to about 5,000 ppm, and most preferably about 1 to about 1,000 ppm.

The peroxygen bleaching composition which can be used directly in water or as an additive in a fully formulated cleaning composition comprises the peroxygen bleaching compound and the peroxygen bleach activator in a weight ratio of bleaching compound to bleach activator of about 1:1 to about 100:1, preferably about 1:1 to about 50:1 and most preferably about 1:1 to about 10:1. The peroxygen bleaching composition can be utilized as an additive to a fully formulated composition at a concentration level of about 1 to about 75 wt. %, preferably about 6 to about 60 wt. % and most preferably about 5 to about 50 wt. % depending upon the type of cleaning composition.

In order to improve the storage shelf life of the peroxygen bleaching composition either the peroxygen bleaching compound, for example, the monopersulfate or the decalindione bleach activator can be encapsulated utilizing any of the conventional encapsulating agents which is water soluble at a preselected temperature. The conventional techniques can be utilized for the encapsulation.

A typical powder form automatic dishwashing composition of the instant invention comprises:

(a) 20 to 70% of a detergent builder salt;

(b) 5 to 40% of an alkali metal silicate;

(c) 0 to 30% of an alkali metal carbonate;

(d) 0 to 6% of an anionic or nonionic surfactant;

(e) 0 to 6% of a foam depressant;

(f) 0 to 4% of an antifilming agent selected from the group consisting of silica, alumina and titanium dioxide;

(g) 0 to 20% of a low molecular polyacrylic acid;

(h) 0 to 20% of at least one enzyme;

(i) 1 to 75% of a peroxygen bleach compound; and (j) 1 to 75% of a decalindione or derivative thereof as bleach activator.

A typical nonaqueous liquid automatic dishwashing composition comprises approximately by weight:

(a) 3 to 20% of an alkali metal silicate;

(b) 0 to 15% of a clay gel thickener;

(c) 0 to 1% of a hydroxypropylcellulose polymer;

(d) 0 to 25% of a low molecular weight polyacrylate polymer;

(e) 0 to 15% of a liquid nonionic surfactant;

(f) 2 to 15% of an alkali metal carbonate;

(g) 0 to 7% of a stablizing system;

(h) 0 to 25% of an alkali metal citrate;

(i) 0 to 20% of at least one enzyme;

(j) 0 to 20% of a nonaqueous liquid carrier;

(k) 1 to 75% of a peroxygen bleaching compound; and (l) 1 to 75% of a decalindione bleach compound activator.

A typical powder form detergent composition comprises approximately by weight:

(a) 0 to 25% of at least one nonionic surfactant;

(b) 0 to 25% of at least one anionic surfactant;

(c) 0 to 40% of a zeolite;

(d) 5 to 45% of at least one builder salt;

(e) 0 to 5% of polyethylene glycol;

(f) 0 to 10% of an alkali metal silicate;

(g) 0 to 10% of a low molecular weight polyacrylate polymer;

(h) 0 to 30% of an alkali metal sulfate;

(i) 1 to 75% of a peroxygen bleaching compound; and (j) 1 to 75% of a decalindione bleaching compound activator.

A typical nonaqueous laundry detergent comprises approximately by weight:

(a) 20 to 70% of a nonionic surfactant;

(b) 0.5 to 20% of a nonaqueous solvent;

(c) 10 to 60% of at least one builder salt;

(d) 0.5% to 1.5% of a foam depressant;

(e) 1 to 75% of a peroxygen bleaching compound; and (f) 1 to 75% of a decalindione bleaching compound activator.

A typical scouring powder composition comprises approximately by weight:

| | |
|---|---|
| (a) White Silex | 90.85 |
| (b) Detergent | 2.0 |
| (c) Soda Ash | 6.0 |
| (d) Decalindione Bleach System | 1.0 |
| (e) Perfume | 0.15 |

A typical nonconcentrated powdered bleach composition comprises approximately by weight:

| | |
|---|---|
| (a) 1 to 75 | Potassium Monopersulfate |
| (b) 1 to 75 | Decalindione |
| (c) 2 to 15% | Sodium carbonate (soda ash) |
| (d) 50-0% | Silex |

A more detailed description and explanation of the ingredients used in the previously defined formulations is as follows:

The bleach activator process of the instant invention is carried out in aqueous solution having a pH of from about 7 to about 12. Outside this pH range, bleaching performance falls off markedly. Since an aqueous solution of the persalts or peracids of the present invention is generally acidic, it is necessary to maintain the requisite pH conditions by utilizing standard buffering agents. A buffering agent is, of course, any non-interfering compound which can alter and/or maintain pH, such as any standard buffering agent or combination. For example, phosphates, carbonates, or bicarbonates which buffer within the 7-12 pH range are useful. Examples of suitable buffering agents include sodium bicarbonate, sodium carbonate, disodium hydrogen phosphate and sodium dihydrogen phosphate. Other buffering agents for any desired pH can be obtained by the skilled artisan from any standard chemistry handbook or textbook. Buffering agents generally comprise from about 1% to about 85% by weight of the instant concentrated bleaching compositions.

The nonionic surfactants that can be used in the compositions are well known.

Nonionic synthetic organic detergents suitable for use herein include ethoxylated propoxylated fatty alcohols which are low-foaming surfactants and are possibly capped. These detergents are characterized by the presence of an organic hydrophobic group and an organic hydrophilic group and are typically produced by the condensation of an organic aliphatic or alkyl aromatic hydrophobic compound with ethylene oxide and/or propyleneoxide (hydrophilic in nature). Almost any hydrophobic compound having a carboxy, hydroxy, amido or amino group with a free hydrogen attached to the oxygen or the nitrogen can be condensed with ethylene oxide or proplylene oxide or with the polyhydration product thereof, polyethylene glycol, to form a nonionic detergent. The length of the hydrophilic or polyoxyethylene chain can be readily adjusted to achieve the desired balance between the hydrophobic and hydrophilic groups. Typical suitable nonionic surfactants are those disclosed in U.S. Pat. Nos. 4,316,812 and 3,630,92.

Preferably, the nonionic detergents are low-foaming polyalkoxylated lipophiles, wherein the desired hydrophile-lipophile balance is obtained by addition of a hydrophilic poly-lower alkoxy group to a lipophilic moiety. A preferred class of nonionic detergents is the poly-lower alkoxylated higher alkanols, wherein the alkanol has 9 to 18 carbon atoms and wherein the number of moles of lower alkylene oxide (of 2 or 3 carbon atoms) is from 3 to 15. It is preferred to employ poly-lower alkoxylated higher alkanols, the alkanol being a fatty alcohol of 9 to 11 or 12 to 15 carbon atoms and containing from 5 to 15 or 5 to 16 lower alkoxy groups per mole. Preferably, the lower alkoxy is ethoxy but in some instances, it may be desirably mixed with propoxy, the latter, if present, usually constituting more than 50% of the mixture. Exemplary of such compounds are those where the alkanol contains 12 to 15 carbon atoms and there are present about 7 ethylene oxide groups per mole.

Useful nonionics are represented by the low foam Plurafac series available from BASF Chemical Company and which are the reaction product of a higher linear alcohol and a mixture of ethylene and propylene oxides, containing a mixed chain of ethylene oxide and propylene oxide, terminated by a hydroxyl group. Examples include Product A(a $C_{13}$-$C_{15}$ fatty alcohol condensed with 6 moles ethylene oxide and 3 moles propylene oxide), Product B (a $C_{13}$-$C_{15}$ fatty alcohol condensed with 7 moles propylene oxide and 4 moles ethylene oxide), and Product C (a $C_{13}$-$C_{15}$ fatty alcohol condensed with 5 moles propylene oxide and 10 moles ethylene oxide). Preferred surfactants are Plurafac LF132 and LF231 which are capped nonionic surfactants. Another liquid nonionic surfactant suitable for use herein is sold under the tradename Lutensol SC 9713.

Synperonic nonionic surfactants available from ICI such as Synperonic LF/D25 are especially preferred for use in formulating the powdered automatic dishwasher detergent compositions of the instant invention.

Other useful surfactants are Neodol 25-7 and Neodol 23-6.5, products of Shell Chemical Company, Inc. The later is a condensation product of a mixture of higher fatty alcohols averaging about 12 to 13 carbon atoms, the number of ethylene oxide groups present averaging about 6.5. The higher alcohols are primary alkanols. Still other examples of suitable detergents include Tergitol 15-S-7 and Tergitol 15-S-9, both of which are linear secondary alcohol ethoxylates made by Union Carbide Corporation. The former is a mixed ethoxylation product of an 11 to 15 carbon atom linear secondary alkanol with seven moles of ethylene oxide and the latter is a similar product but with nine moles of ethylene oxide.

Also useful in the present compositions as a component of the nonionic detergent are the higher molecular weight nonionics, such as Neodol 45-11, which are similar ethylene oxide condensation products of higher fatty alcohols, with the higher fatty alcohol having 14 to 15 carbon atoms and the number of ethylene oxide groups per mole being about 11. Such products are made by Shell Chemical Company.

In the preferred poly-lower alkoxylated higher alkanols, in order to obtain the best balance of hydrophilic and lipophilic moieties, the number of lower alkoxy groups will usually be from 40% to 100% of the number of carbon atoms in the higher alcohol, preferably 40 to 60% thereof and the nonionic detergent will preferably contain at least 50% of such preferred poly-lower alkoxy higher alkanol.

Alkylpolysaccharide surfactants which can be used alone or in combination with the aforementioned surfactants are those having a hydrophobic group containing from about 8 to 20 carbon atoms, preferably from about 10 to about 16 carbon atoms, most preferably from 12 to 14 carbon atoms, and a polysaccharide hydrophilic group containing from 1.5 to about 10, preferably from about 1.5 to 4 and most preferably from 1.6 to 2.7 saccharide units (e.g., galactoside, glucoside, fructoside, glucosyl, fructosyl, and/or galactosyl units). Mixtures of saccharide moieties may be present in the alkyl polysaccharide surfactants. The alkylpolysaccharide surfactants correspond to the following formula:

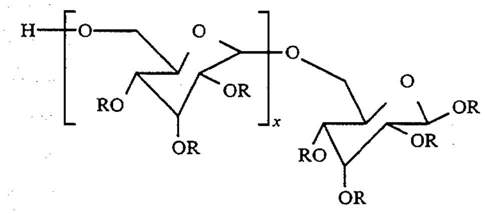

In the formula, x indicates the number of saccharide units in a particular alkylpolysaccharide surfactant. For a particular alkylpolysaccharide molecule, x can only represent an integral value. Any physical sample can be characterized by the average value of x and this average value can assume non-integral values. As used in this application, the value of x is to be understood as designating an average value. The hydrophobic group (R) can be attached at the 2-, 3-, or 4- positions rather than at the 1- position (resulting in, for example, a glucosyl or galactosyl as opposed to a glucoside or galactoside). However, attachment at the 1-position, i.e., gluocsides, galactosides, fructosides, etc., is preferred. In the preferred product, the additional saccharide units are predominately attached to the previous saccharide unit's 2-position. Attachment through the 3-, 4-, and 6- positions can also occur. Optionally and less desirably, there can be a polyalkoxide chain joining the hydrophobic moiety (R) and the polysaccharide chain. The preferred alkoxide moiety is ethoxide.

Typical hydrophobic groups include alkyl groups, either saturated or unsaturated, branched or unbranched containing from about 8 to about 20, preferably from about 10 to about 16 carbon atoms. Preferably, the alkyl group contains up to 3 hydroxy groups and/or the polyalkoxide chain contains up to about 30, preferably less than 10, most preferably 0, alkoxide moieties.

Suitable alkyl polysaccharides are decyl, dodecyl, tetradecyl, pentadecyl, hexadecyl, and octadecyl, di-tri-, tetra-, penta-, and hexaglucosides, galactosides, lactosides, fructosides, fructosyls, lactosyls, glucosyls and/or glactosyls and mixtures thereof.

The alkyl monosaccharides are relatively less soluble in water than the higher alkylpolysaccharides. When used in admixture with alkylpolysaccharides, the alkyl monosaccharides are solubilized to some extent. The use of alkyl monsaccharides in admixture with alkylpolysaccharides is a preferred mode of carrying out the invention. Suitable mixtures include coconut alkyl, di-tri-tetra-, and pentaglucosides and tallow alkyl tetra-penta-, and hexaglucosides.

The preferred alkyl polysaccharides are alkyl polyglucosides having the formula:

$(R_2O)C_nH_{2n}O)_t(Z)_x$ wherein Z is derived from glucose, R is a hydrophobic group selected from alkyl, alkylphenyl, hydroxyalkylphenyl, and mixtures thereof in which said alkyl groups contain from about 10 to about 18, preferably from 12 to 14 carbon atoms; n is 2 or 3 preferably 2, r is from 0 to about 10, preferably 0; and x is from 1.5 to about 8, preferably from 1.5 to 4, most preferably from 1.6 to 2.7. These compounds are prepared by reacting a long chain alcohol ($R_2OH$) with glucose, in the presence of an acid catalyst to form the desired glucoside. Alternatively, the alkylpolyglucosides can be prepared by a two step procedure in which a short chain alcohol ($C_{1-6}$) is reacted with glucose or a polyglucoside (x=2 to 4) to yield a short chain alkyl glucoside (x=1 to 4) which can in turn be reacted with a longer chain alcohol ($R_2OH$) to displace the short chain alcohol and obtain the desired alkylpolyglucoside. If this two step procedure is used, the short chain alkylglucoside content of the final alkylpolyglucoside material should be less than 50%, preferably less than 10%, more preferably less than 5%, and most preferably 0% of the alkylpolyglucoside.

The amount of unreacted alcohol (the free fatty alcohol content) in the desired alkylpolysaccharide surfactant is preferably less than 2%, more preferably less than about 0.5% by weight of the total of the alkylpolysaccharide. For some uses, it is desirable to have the alkyl monosaccharide content less than about 10%.

As used herein, "alkyl polysaccharide surfactant" is intended to represent both the preferred glucose and galactose derived surfactants as well as the less preferred alkyl polysaccharide surfactants. As used in this application the term "alkyl polyglusoside" includes alkyl-polyglycosides because the stereo chemistry of the saccharide moiety is changed during the preparation reaction.

An especially preferred APG glycoside surfactant is APG 625 glycoside manufactured by the Henkel Corporation of Ambler, Pa. APG 25 is a nonionic alkyl polyglycoside characterized by the formula:

$C_nH_{2n+1}O(C_6H_{10}O_5)_{2x}H$ wherein n=10 (2%); n=12 (65%); n=14 (21–28%); n=16 (4–8%) and n=18(0.5%) and x(degree of polymerization)=1.6. APG 625 has: a pH of 6–8(10% of APG 625 in distilled water); a specific gravity at 25° C. of 1.1 grams/ml; a density at 25° C. of 9.1 kgs/gallon; a calculated HLB of about 12.1 and a Brookfield viscosity at 35° C., 21 spindle, 5–10 RPM of about 3,000 to about 7,000 cps. Mixtures of two or more of the liquid nonionic surfactants can be used advantageously.

Other detergent active materials useful in the composition are the organic anionic, amine oxide, phosphine oxide, sulphoxide and betaine water dispersible surfactants, the first mentioned anionics being most preferred. Particularly preferred surfactants herein are the linear or branched alkali metal mono- and/or di- ($C_8$–$C_{14}$) alkyl diphenyl oxide mono- and/or di-sulphates, commercially available, for example, as DOWFAX® 3B-2 and DOWFAX 2A-1. In addition, the surfactant should be compatible with the other ingredients of the composition. Other suitable organic anionic, non-soap surfactants include the primary alkylsulphates, alkylsulphonates, alkylarylsulphonates and sec.-alkylsulphates. Examples include the sodium $C_{10}$–$C_{18}$ alkylsulphates such as sodium. dodecylsulphate and sodium tallow alcoholsulphate; sodium $C_{10}$–$C_{18}$ alkanesulphonates such as sodium hexadecyl-1-sulphonate and sodium $C_{12}$–$C_{18}$l alklylbenzenesulphonates, for example sodium dodecylbenzenesulphonate. The corresponding potassium salts may also by employed.

Other suitable surfactants or detergents, suitable for use in the invention include the amine oxide surfactants typically of the structure $R_2R_1NO$, in which $R_2$ represents a lower alkyl group, for instance, methyl, and $R_1$ represents a long chain alkyl group having from 8 to 22 carbon atoms, for instance, a lauryl, myristyl, palmityl or cetyl group. Instead of an amine oxide, a corresponding surfactant phosphine oxide $R_2R_1PO$ or sulphoxide $RR_1SO$ can be employed. Betaine surfactants are typically of the structure $R_2R_1N^+R''CCO$—, in which each R represents a lower alkylene group having from 1 to 5 carbon atoms. Specific examples of these surfactants include lauryl-dimethylamine oxide, myristyl-dimethylamine oxide, the corresponding phosphine oxides and sulphoxides, and the corresponding betaines, including dodecyldimethylammonium acetate, tetradecyldiethylammonium pentanoate, hexadecyldimethylammonium hexanoate and the like. To ensure biodegradability, the alkyl groups in these surfactants should be linear, and such compounds are preferred.

Surfactants of the foregoing type, all well known in the art, are described, for example, in U.S. Pat. Nos. 3,985,668 and 4,271,030. If chlorine bleach is not used, then any of the well-known low-foaming nonionic surfactants such as alkoxylated fatty alcohols, e.g., mixed ethylene oxide-propylene oxide condensates of $C_8$–$C_{22}$ fatty alcohols, can also be used.

Foam inhibition is important to increase dishwasher and laundry machine efficiency and minimize destabilizing effects which might occur due to the presence of excess foam within the washer during use. Foam may be reduced by suitable selection of the type and/or amount of detergent active material, the main foam-producing component. The degree of foam is also somewhat dependent on the hardness of the wash water in the machine whereby suitable adjustment of the proportions of the builder salts such as NaTPP which has a water softening effect, may aid in providing a degree of foam inhibition. However, it is generally preferred to include a chlorine bleach stable foam depressant or inhibitor. Particularly effective are the alkyl phosphoric acid esters of the formula:

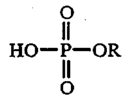

In the above formula, one or both R groups represents independently a $C_{12}$–$C_{20}$ alkyl or ethoxylated alkyl group. The ethoxylated derivatives of the ester, for example, the condensation products of one mole of ester with from 1 to 10 moles, preferably 2 to 6 moles, more preferably 3 or 4 moles, ethylene oxide, can also be used. Some examples of alkyl phosphoric acid esters that are commercially available, include the products SAP from Hooker and LPKN-158 from Knapsack. Mixtures of the esters, or any other chlorine bleach stable types, or mixtures of mono- and di-esters of the same type, may be employed. Especially preferred is a mixture of mono- and di-$C_{16}$–$C_{18}$ alkyl acid phosphate esters such as monostearyl/distearyl acid phosphates 1.2/1, and the 3 to 4 mole ethylene oxide condensates thereof. When used, proportions of 0 to 1.5 weight percent, preferably 0.05 to 0.5 weight percent, of foam suppressant in the composition is typical, the weight ratio of detergent active component to foam suppressant generally ranging from about 10:1 to 1:1 and preferably about 5:1 to 1:1. Additional defoamers which may be used include, for example, the known silicones, such as are available from Dow Chemical. In addition, it is an advantageous feature of this invention that many of the stabilizing salts, such as the stearate salts, for example, aluminum stearate, when included, are also effective as foam inhibitors or suppressants.

Some specific examples of the alkali metal detergent builder salts used in the composition include the polyphosphates, such as alkali metal pyrophospate, alkali metal tripolyphosphate, alkali metal metaphosphate, and the like, for example, sodium or potassium tripolyphosphate (hydrated or anhydrous), tetrasodium or tetrapotassium pyrophosphate, sodium or potassium hexa-metaphosphate, trisodium or tripotassium orthophosphate, and the like. The phosphate builders, where not precluded due to local regulations, are preferred and mixtures of tetrapotassium pyrophosphate (TKPP) and sodium tripolyphosphate (NaTPP) (especially the hexahydrate) are especially preferred. Typical ratios of NaTPP to TKPP are from about 2:1 to 1:8, preferably from about 1:1.1 to 1:6. The total amount of detergent builder salts is preferably from about 5 to 45% by weight, preferably from about 15 to 35%, most preferably from about 18 to 30% by weight of the composition.

In combination with the builder salts there is optionally used a low molecular weight noncrosslinked polyacrylate having a molecular weight of about 1,000 to about 100,000, more preferably about 2,000 to about 80,000. A preferred low molecular weight polyacrylate is Norasol LMW45ND manufactured by Norsohaas and having a molecular weight of about 4,500. These low molecular weight polyacrylates are employed at a concentration of about 0 to 15 wt. %, preferably 0.1 to 10 wt. %.

Other useful low molecular weight noncrosslinked polymers are Acusol TM 640D sold by Rohm & Haas and Norasol QR1014 sold by Norshohaas having a GPC molecular weight of 10,000.

The compositions can also contain a nonphosphate builder system comprised of a mixture of phosphate-free particles formed from a builder salt and a low molecular weight polyacrylate. A preferred solid builder salt is an alkali metal carbonate such as sodium carbonate or sodium citrate or a mixture of sodium carbonate and sodium citrate. When a mixture of sodium carbonate and sodium citrate is used, a weight ratio of sodium carbonate to sodium citrate of about 9:1 to about 1:9, preferably about 3:1 to about 1:3 is used.

Other builder salts which can be mixed with the sodium carbonate and/or sodium citrate are gluconates, phosphonates, and nitriloacetic acid salts. In conjunction with the builder salts, there are optionally used low molecular weight polyacrylates having a molecular weight of about 1,000 to about 100,000 and preferably about 2,000 to about 80,000. Preferred low molecular weight polyacrylates include Sokalan TM CP45 and Sokalan TM CP5 manufactured by BASF having a molecular weight of about 70,000. Another preferred low molecular weight polyacrylate is Acrysol TM LMW45ND manufactured by Rohm and Haas having a molecular weight of about 4,500.

Sokalan TM CP45 is a partially neutralized copolymer of methacrylic acid and maleic anhydride. For use herein, the copolymer should have a water absorption at 38° C. and 78 percent relative humidity of less than about 40 percent and preferably less than about 30 percent. Sokolan TM CP5 is the totally neutralized copolymer of methacrylic acid and maleic acid anhydride. Sokolan TM CP45 is classified as a suspending and anti-deposition agent. It has a low hygroscopicity as a result of a decreased hydroxyl group content. An objective is to use suspending and anti-redeposition agents that exhibit a low hygroscopicity. Copolymerized polyacids have this property, and particularly when partially neutralized. Aucsol TM 640ND available from Rohm & Haas is another useful suspending and anti-redeposition agent. Another example of a suitable builder is Sokalan TM 9786X which is a copolymer of silicates and is described in British Patent No. 1,504,168, U.S. Pat. No. 4,409,136 and Canadian Patent Nos. 1,072,835 and 1,087,477. Illustrative of the amorphous zeolites useful herein are those described in Belgium Patent No. 835,351. The zeolites generally have the formula $$(M_2O)x(Al_2O_3)y(SiO_2)zwH_2O$$

wherein x is 1, y is from 0.8 to 1.2 and preferably 1, z is from 1.5 to 3.5 or higher and preferably 2 to 3 and w is from 0 to 9, preferably 2.5 to 6 and M is preferably sodium. A typical zeolite is type A or similar structure, with type 4A particularly preferred. The preferred aluminosilicates have calcium ion exchange capacities of about 200 milliequivalents per gram or greater, e.g., 400 meq/g.

The alkali metal silicates serve as anti-corrosion agents functioning to make the composition anti-corrosive to eating utensils and to automatic dishwashing machine parts. Sodium silicates of $Na_2O/SiO_2$ ratios of from 1:1 to 1:3.4 especially about 1:2 to 1:3 are preferred. Potassium silicates of the same ratios can also be used. The preferred silicates are sodium disilicate (hydrated or anhydrous) and sodium metasilicate.

Thickening agents that can be used to ensure the physical stability of the suspension and to enhance its viscosity are those that will swell and develop thixotropic properties in a nonaqueous environment. These include organic polymeric materials and inorganic and organic modified clays. Essentially, any clay can be used as long as it will swell in a nonaqueous medium and exhibits thixotropic properties. A preferred clay is bentonite. A swelling agent is used with the bentonite clay. The preferred swelling agent is a combination of propylene carbonate and tripropylene glycol methyl ether. However, any other substance that will cause bentonite to swell in a nonaqueous environment and to develop thixotropic properties can be used.

The nonaqueous liquid carrier materials that can be used for formulating nonaqueous liquid compositions include the higher glycols, polyglycols, polyoxides and glycol ethers. Suitable substances are propylene glycol, polyethylene glycol, polypropylene glycol, diethylene glycol monoethyl ether, diethylene glycol monopropyl ether, diethylene glycol monobutyl ether, tripropylene glycol methyl ether, propylene glycol methyl ether (PM), dipropylene glycol methyl ether (DPM), propylene glycol methyl ether acetate (PMA), dipropylene glycol methyl ether acetate (DPMA), ethylene glycol n-butyl ether and ethylene glycol n-propyl ether. A preferred nonaqueous carrier of the instant invention is polyethylene glycol 200 (PEG200) or polyethylene glycol 300 (PEG300).

Other useful solvents are ethylene oxide/propylene oxide, liquid random copolymers such as the Synalox solvent series from Dow Chemical (e.g. Synalox 50-50B). Other suitable solvents include propylene glycol ethers such as PnB, DPnB and TPnB (propylene glycol mono n-butyl ether, diproplylene glycol and tripropylene glycol mono-n-butyl ethers) sold by Dow Chemical under the trademark Dowanol. Also tripropylene glycol mono methyl ether "TPM Dowanol" available from Dow Chemical is suitable. Another useful series of solvents are supplied by CCA Biochem of Holland as, for example, Plurasolv ®ML, Plurasolv ®LS(s), Plurasolv ®EL, Plurasolv ®IPL and Plurasolv ®BL.

Mixtures of PEG solvent with Synalox or PnB, DPnB, TPnB and TPM solvents are also useful. Preferred mixtures are PEG 300/Synalox 50-50B and PEG 300/TPnB in weight ratios of about 95:5 to 20:80, more preferably of about 90:10 to 50:50. EP/PO capped nonionic surfactants can be used as a liquid solvent carrier and an example of such a nonionic surfactant is Plurafac LF/132 sold by BASF.

The system used in the instant compositions to ensure phase stability (stablizing system) can comprise a finely divided silica such as Cab-O-Sil M5, Cab-O-Sil EH5, Cab-O-Sil TS720 or Aerosil 200. The stabilizer is used in a concentration level of about 0 to about 4.0 weight percent, and preferably about 0.5 to about 3.0 weight %. There can also be employed as a stablizing system mixtures of finely divided silica such as Cab-O-Sil and nonionic associative thickeners such as Dapral T210, T212 (Akzo) which are low molecular weight dialkyl polyglycol ethers with a dumbbell-like structure or Pluracol TH 916 and TH 922 (BASF) associative thickeners having star-like structures with a hydrophilic core and hydrophobic tail. These thickeners are used at concentration levels of about 0 to about 5.0 weight percent together with about 0 to about 2.0 weight percent of finely divided silica. Other useful stablizing systems are blends of organoclay gel and hydroxpropyl cellulose polymer (HPC). A suitable organoclay is Bentone NL27 sold by NL Chemical. A suitable cellulose polymer is Klucel M cellulose having a molecular weight of about 1,000,000 sold by Aqualon Company. Bentone gel contains 9 percent Bentone NL 27 powder (100 percent active), 88 percent TPM solvent (tripropylene glycol mono methyl ether) and 3 percent propylene carbonate (polar additive). The organic modified clay thickener gels are used at concentration levels of about 0.0 weight percent to about 15 weight percent in conjunction with Klucel M at concentration levels of about 0 to about 0.6 weight percent, preferably about 0.2 weight percent to about 0.4 weight percent. Another useful thickening agent is a high molecular weight long chain alcohol such as Unilin TM 425 sold by Petrolite Corp.

The detergent formulation can also contain a mixture of a proteolytic enzyme and an amylotytic enzyme and optionally, a lipolytic enzyme that serves to attack and remove organic residues on glasses, plates, pots, pans and eating utensils. Proteolytic enzymes attack protein residues, lipolytic enzymes fat residues and amylotytic enzymes starches. Proteolytic enzymes include the protease enzymes subtilism, bromelin, papain, trypsin and pepsin. Amylolytic enzymes include amylase enzymes. Lipolytic enzymes include the lipase enzymes. The preferred amylase enzyme is available under the name Maxamyl, derived from Bacillus licheniformis and is available from Gist-Brocades of the Netherlands in the form of a nonaqueous slurry (18 wt. % of enzyme) having an activity of about 40,000 TAU/g. The preferred protease enzyme is available under the name Maxatase derived from a novel Bacillus strain designated "PB92", a culture of the Bacillus is deposited with the Laboratory for Microbiology of the Technical University of Delft, has the number OR-60, and is supplied by Gist-Brocades, of the Netherlands in a nonaqueous slurry (22 wt. % of enzyme/activity of about 400,000 DU/g. Preferred enzyme activities per wash are Maxatase-100-800 KDU per wash and Maxamyl-1,000-8,000 TAU per wash.

The weight ratio of the slurry of the proteolytic enzyme to the amylolytic in the nonaqueous liquid automatic dishwasher detergent compositions is about 25:1 to about 1:1, and preferably about 15:1 to about 1.5:1.

Other conventional ingredients may be included in these compositions in small amounts, generally less than about 3 weight percent, such as perfume, hydrotropic agents such as the sodium benzene, toluene, xylene and cumene sulphonates, preservatives, dyestuffs and pigments and the like, all of course being stable to bleaching compounds and high alkalinity. Especially preferred for coloring are the chlorinated phythalocyanines and polysulphides of aluminosilicate which provide, respectively, pleasing green and blue tints. $TiO_2$ may be employed for whitening or neutralizing off-shades.

The invention may be put into practice in various ways and a number of specific embodiments of the bleaching compositions of the instant invention are set forth below for illustrating the invention.

In order to test the efficacy of the claimed compositions the following compositions were prepared and the described procedures performed. A solution of 350 mgms of potassium monopersulfate (Oxone) and 1.0 gram of Fab Ultra detergent in one liter of water was prepared and to the solution of the Oxone and detergent Fab Ultra, there was added 100 mgms of 1,5-decalindione. (Solution A)-Composition of the Invention. A solution was prepared from 350 mgms of potassium monopersulfate, 1 gram of Fab Ultra in 1 liter of water, 100 mgms of 1,4-cyclohexanedione monoethylene ketal added to the resultant solution. (Solution B)-Composition of Patent Application Serial No. 7/870,362. A solution was prepared from 1 gram of Fab Ultra and 350 mg Oxone in 1 liter of water (Solution C)-Control.

Bleaching tests were performed in a six bucket (1 liter) terg-o-tometer at 80° F. and 120° F. Tests were run in tap water. Solution C acted as a control.

The dioxiranes were generated in situ by the addition of Oxone (0.35 gms) and diketone or decalindione (0.10 gms) to the terg-o-tometer bucket which contained the Fab Ultra detergent. After 30 seconds of agitation of the above solution, the stained swatches were added to the solution and agitation was continued for 15 minutes. The stains were then rinsed in tap water, dried and their reflectance measured on a reflectometer to determine average soil removal (% ASR).

The following four stained swatches were evaluated for bleaching in the test:

Grape juice on dacron (65/cotton (35)
Blueberry pie on cotton percale
Red wine-114* on heavy cotton
Instant coffee on cotton percale Determining the % Average Soil Removal The % Average Soil Removal (% ASR) value is calculated by averaging the individual % Soil Removal (% SR) values of the four stains evaluated. The % Soil Removal (% SR) of a stained swatch was determined by manipulating its reflectance values which are measured from the swatch both before and after washing. A reflectance value is the amount of light that a surface (such as that of a swatch will reflect. The following example will illustrate this protocol. Red wine (EMPA-114) stained swatches were bleached in the Dioxirane system (Bicyclic diketone-Oxone-A) or cyclohexyldione monoethylene ketal-B using the procedure above. Table 1 provides the measured reflectance values of the swatches without stain (No Soil), with the stain (Soiled), and after washing (Washed). For each stain there are two swatches evaluated in order that there be an average value calculated.

*Commercial stain sold as EMPA-114 by Test Fabrics

Summary of the Dioxirane Bleach Efficacy Comparisons in Terg-O-Tometer at 80° and 120° F.; Tap Water; 15 min.

TABLE 1

| Activator (System | % Soil Removal Values at T = 80° F. Grape Juice (65D/35C) | Blueberry Pie (Cotton Per) | Red Wine* Empa-114 (Heavy Cotton) | Coffee/Tea (Cotton Per) | Average of 4-Stains |
|---|---|---|---|---|---|
| Bicyclic (A) Diketone | 59 ± 1 | 89 ± 1 | 43 ± 2 | 73 ± 1 | 65 ± 1 |
| Cyclohexyl (B) Dione Monoketal U.S. Pat. Filing 7/870362 | 58 ± 1 | 86 ± 1 | 39 ± 1 | 69 ± 7 | 63 ± 2 |
| Oxone (C) | 37 ± 6 | 38 ± 10 | 35 ± 3 | 26 ± 6 | 34 ± 4 |

(A) Decalin-1, 5-dione (100% active) (100 ppm, or 100 mg/l), FAB Ultra (1000 ppm, or 1 gm/l), Oxone (350 ppm, or 350 mg/l).
(B) 1,4-Cyclohexanedione, monoethylene ketal (100 ppm, or 100 mg/l), FAB Ultra (1000 ppm, or 1 gm/l), Oxone (350 ppm, or 350 mg/l).
(C) FAB Ultra (1000 ppm, or 1 gm/l), Oxone (350 ppm, or 350 mg/l).

EXAMPLE II

The bleaching efficacy of the bicyclic diketone (A) was also evaluated in comparison to the cyclohexyldione monoethylene ketal (B) of copending application at a temperature of 120° F. The results are set out in Table 2. In all instance the bicyclic diketone was more effective in stain removal.

TABLE 2

| Activator System | % Soil Removal Values at T = 120° F. Grape Juice (65D/35C) | Blueberry Pie (Cotton Per) | Red Wine* Empa-114 (Heavy Cotton) | Coffee/Tea (Cotton Per) | Average of 4-Stains |
|---|---|---|---|---|---|
| Bicyclic (A) Diketone | 55 ± 4 | 89 ± 1 | 46 ± 2 | 80 ± 4 | 68 ± 2 |
| Cyclohexyl (B) Dione Monoketal U.S. Pat. Filing 7/870362 | 27 ± 2 | 75 ± 2 | 40 ± 2 | 51 ± 1 | 48 ± 1 |

(A) Decalin-1, 5-dione, 100% active (100 ppm, or 100 mg/l), FAB Ultra (1000 ppm, or 1 gm/l), Oxone (350 ppm, or 350 mg/l).
(B) 1,4-Cyclohexanedione, monoethylene ketal (100 ppm, or 100 mg/l), FAB Ultra (1000 ppm, or 1 gm/l), Oxone (350 ppm, or 350 mg/l).

TABLE 3

| Activator System | % Soil Removal Values at T = 80° F. Grape Juice (65D/35C) | Blueberry Pie (Cotton Per) | Red Wine* Empa-114 (Heavy Cotton) | Coffee/Tea (Cotton Per) | Average of 4-Stains |
|---|---|---|---|---|---|
| Bicyclic (A) Diketone | 54 ± 2 | 74 ± 2 | 33 ± 1 | 86 ± 5 | 62 ± 2 |
| Cyclohexyl (B) Dione Monoketal U.S. Pat. Filing 7/870362 | 65 ± 2 | 86 ± 1 | 41 ± 1 | 89 ± 2 | 70 ± 1 |
| SNOBS (C) | 51 ± 1 | 57 ± 3 | 58 ± 3 | 55 ± 5 | 55 ± 2 |

(A) Methyl-decalin-1, 6-dione, 100% active (100 ppm, or 100 mg/l), FAB Ultra (1000 ppm or 1 gm/l), Oxone (350 ppm, or 350 mg/l).
(B) 1,4-Cyclohexanedione, monoethylene ketal, 100% Active (100 ppm, or 100 mg/l), FAB Ultra (1000 ppm, or 1 gm/l), Oxone (350 ppm, or 350 mg/l).
(C) SNOBS (106 mg), 94.3% Active (100 mg, 0.297 mmol), FAB Ultra (1000 ppm, or 1 gm/l), Sodium Perborate (127 ppm, 4:1).

TABLE 4

| Activator System | % Soil Removal Values at T = 120° F. Grape Juice (65D/35C) | Blueberry Pie (Cotton Per) | Red Wine* Empa-114 (Heavy Cotton) | Coffee/Tea (Cotton Per) | Average of 4-Stains |
|---|---|---|---|---|---|
| Bicyclic (A) Diketone | 63 ± 2 | 82 ± 2 | 51 ± 1 | 91 ± 3 | 72 ± 1 |
| Cyclohexyl (B) Dione Monoketal U.S. Pat. Filing 7/870362 | 48 ± 4 | 71 ± 5 | 47 ± 1 | 77 ± 6 | 61 ± 4 |
| SNOBS (C) | 58 ± 2 | 64 ± 3 | 57 ± 2 | 78 ± 4 | 64 ± 2 |

(A) Decalin-1, 5-dione, 100% active (100 ppm, or 100 mg/l), FAB Ultra (1000 ppm, or 1 gm/l), Oxone (350 ppm, or 350 mg/l).
(B) 1,4-Cyclohexanedione, monoethylene ketal (100 ppm, or 100 mg/l), FAB Ultra (1000 ppm, or 1 gm/l), Oxone (350 ppm, or 350 mg/l).
(C) SNOBS (106 mg), 94.3% Active (100 mg, 0.297 mmol), FAB Ultra (1000 ppm, or 1 gm/l), Sodium Perborate (127 ppm, 4:1).

What is claimed is

1. A peroxygen bleaching composition which comprises approximately by weight a mixture of:
(a) about 1 to about 75% a peroxygen bleaching compound; and
(b) about 1 to about 75% of peroxygen bleaching compound activator which is characterized by the formula:

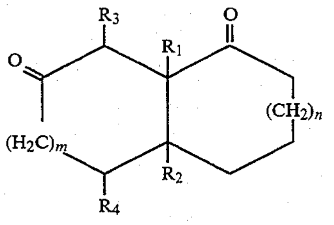

or

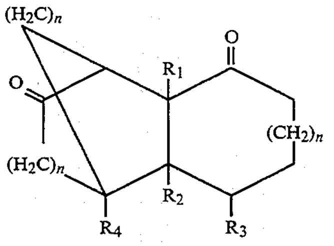

wherein $R_1$, $R_2$, $R_3$ and $R_4$ are each a member selected from the group consisting of hydrogen, alkyl having about 1 to about 8 carbon atoms, aryl having about 6 to about 12 carbon atoms, alkylaryl having 7 to 12 carbon atoms, fluorine, chlorine, bromine, and nitrogen, m is 0, 1, 2 or 3 and n is 0, 1, 2 or 3.

2. A peroxygen bleaching composition according to claim 1, wherein said peroxygen bleaching compound is an inorganic peroxygen bleaching compound.

3. A peroxygen bleaching composition according to claim 2, wherein said inorganic peroxygen bleaching compound is a member selected from the group consisting of monoperoxysulfates and monoperoxyphosphates.

4. A peroxygen bleaching composition according to 2, wherein said inorganic peroxygen bleaching compound is a monoperoxysulfate.

5. A peroxygen bleaching composition according to claim 2 wherein said inorganic peroxygen bleaching compound is potassium mono-peroxysulfate.

6. A peroxygen bleaching composition according to claim 1 wherein each of said peroxygen bleaching compound and said peroxygen bleaching compound activator are present in an amount of about 5 to about 60 weight %.

7. A peroxygen bleaching composition according to claim 1 wherein each of said peroxygen bleaching compounds and said peroxygen bleaching compound activator are present in an amount of about 5 to about 50 weight %.

8. A peroxygen bleaching composition according to claim 1, wherein said mixture is dissolved in water at a concentration of about 0.050 to about 10 grams of said mixture per liter of water.

9. A peroxygen bleaching composition according to claim 1 further including at least one non aqueous liquid carrier, said mixture of said inorganic peroxygen bleaching compound and wherein said peroxygen bleaching compound activator is present in a concentration of about 0.05 to about 10 wt. %.

10. A peroxygen bleaching composition according to claim 1 further including at least one member selected from the following: antifoam agents, thickening agents, surfactants, fabric softening agents, antistatic agents, stablizers, buffering agents, inorganic builder salts, suspending and antideposition agents, alkali metal silicates, enzymes, anticorrosion agents, buffers, stabilizing agents, preservatives, dyestuffs and pigments.

11. A bleaching composition according to claim 1 additionally including a non-aqueous carrier.

12. A bleaching solution comprising water and about 10 to about 1,000 ppm of a composition according to claim 1.

13. A bleaching solution according to claim 12 including at least one member selected from the group consisting of nonaqueous liquid carriers, surfactants, antifoam agents, thickeners, fabric softening agents, antistatic agents, stablizers, suspending and antideposition agents, inorganic builder salts, enzymes, buffers, anticorrosion agents, preservatives, dyestuffs and pigments alkali metal silicates.

14. A bleaching composition in powder form comprising by weight:
(a) 20 to 70% of a detergent builder salt;
(b) 5 to 40% of an alkali metal silicate;
(c) 0 to 30% of an alkali metal carbonate;
(d) 0 to 6% of an anionic or nonionic surfactant;
(e) 0 to 6% of a foam depressant;
(f) 0 to 4% of an anti filming agent selected from the group consisting of silica, alumina and titanium dioxide;
(g) 0 to 20% of a low molecular polyacrylic acid;
(h) 0 to 20% of at least one enzyme;

(i) 1 to 75% of a peroxygen bleach compound; and (j) 1 to 75% of a decalindione or derivative thereof as bleach activator.

15. A bleaching composition in a nonaqueous liquid automatic dishwashing form comprising by weight:

(a) 3 to 20% of an alkali metal silicate;

(b) 0 to 15% of a clay gel thickener;

(c) 0 to 1% of a hydroxypropycellulose polymer;

(d) 0 to 25% of a low molecular weight polyacrylate polymer;

(e) 0 to 15% of a liquid nonionic surfactant;

(f) 2 to 15% of an alkali metal carbonate;

(g) 0 to 7% of a stablizing system;

(h) 0 to 25% of an alkali metal citrate;

(i) 0 to 20% of at least one enzyme;

(j) 0 to 20% of a nonaqueous liquid carrier;

(k) 1 to 75% of a peroxygen bleaching compound; and (l) 1 to 75% of a decalindione bleach compound activator.

16. A bleaching detergent in powder form comprising by weight:

(a) 0 to 25% of at least one nonionic surfactant;

(b) 0 to 25% of at least one anionic surfactant;

(c) 0 to 40% of a zeolite;

(d) 5 to 45% of at least one builder salt;

(e) 0 to 5% of polyethylene glycol;

(f) 0 to 10% of an alkali metal silicate;

(g) 0 to 10% of a low molecular weight polyacrylate polymer;

(h) 0 to 30% of an alkali metal sulfate;

(i) 1 to 75% of a peroxygen bleaching compound; and (j) 1 to 75% of a decalindione bleaching compound activator.

17. A bleaching laundry detergent composition in nonaqueous form comprising by weight:

(a) 20 to 70% of a nonionic surfactant;

(b) 0.5 to 20% of a nonaqueous solvent;

(c) 10 to 60% of at least one builder salt;

(d) 0.5% to 1.5% of a foam depressant;

(e) 1 to 75% of a peroxygen bleaching compound; and (f) 1 to 75% of a decalindione bleaching compound activator.

18. A method for cleaning soiled fabrics by bleaching which comprises adding to an aqueous wash liquor the composition of claim 1 in a sufficient amount to clean said soiled fabrics.

19. A method for removing stains on hard surfaces by bleaching which comprises contacting said stained surface with an effective amount of a composition according to claim 1.

20. A method according to claim 19 wherein said composition is present in an aqueous medium.

21. A method for inhibiting dye transfer from taking place from the aqueous medium in which soiled fabrics are being cleaned by bleaching to the fabrics which comprises adding to the aqueous washing medium an amount of the composition of claim 1 in sufficient amount to inhibit dye transfer.

22. A method for activating a peroxygen bleach compound present in aqueous solution which comprises adding an effective amount of an activator selected from the group consisting of

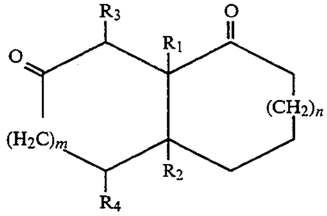

and

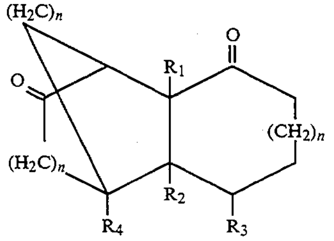

to said aqueous solution containing said peroxygen bleaching compound.

23. A method according to claim 22 wherein said peroxygen bleaching compound is a monopersulfate salt.

24. A peroxygen bleaching composition which comprises approximately by weight a mixture of:

(a) about 1 to about 75% of a peroxygen bleaching compound; and (b) about 1 to about 75% of a peroxygen bleaching compound activator which has a cyclic structure selected from the group consisting of:

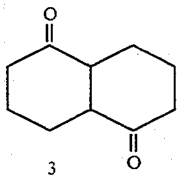

3

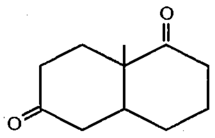

4

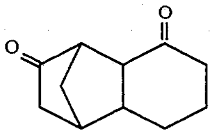

+Isomers

5

25. A bleaching composition according to claim 24 wherein said bleaching compound activator is decalin-1,5-dione.

26. A bleaching composition according to claim 24 wherein said bleaching compound activator is methyldecalin 1,6-dione.

27. A bleaching composition according to claim 24 wherein said bleaching compound activator is a tricyclic dione.

* * * * *